(12) United States Patent
Paakinaho et al.

(10) Patent No.: US 9,393,060 B2
(45) Date of Patent: Jul. 19, 2016

(54) MEDICAL DEVICE AND ITS MANUFACTURE

(75) Inventors: Kaarlo Paakinaho, Tampere (FI); Harri Heino, Tampere (FI); Pertti Tormala, Tampere (FI); Timo Allinniemi, Lampäälä (FI)

(73) Assignee: Bioretec Oy, Tampere (FI)

( * ) Notice: Subject to any disclaimer, the term of this patent is extended or adjusted under 35 U.S.C. 154(b) by 1097 days.

(21) Appl. No.: 12/329,044

(22) Filed: Dec. 5, 2008

(65) Prior Publication Data

US 2009/0149856 A1 Jun. 11, 2009

(30) Foreign Application Priority Data

Dec. 5, 2007 (FI) .................................. 20075881

(51) Int. Cl.
*A61B 17/56* (2006.01)
*A61B 17/86* (2006.01)
(Continued)

(52) U.S. Cl.
CPC .............. *A61B 17/866* (2013.01); *A61L 31/06* (2013.01); *A61L 31/14* (2013.01); *A61L 31/148* (2013.01); *A61B 17/66* (2013.01); *A61B 17/72* (2013.01); *A61B 17/7266* (2013.01); *A61B 17/7275* (2013.01); *A61B 2017/00004* (2013.01);
(Continued)

(58) Field of Classification Search
CPC ....... A61L 31/06; A61L 31/14; A61L 31/148; C08L 67/04; A61B 17/56; A61B 17/66; A61B 17/72; A61B 17/7266; A61B 17/7275; A61B 17/866; A61B 2017/00004; A61B 2017/00867; A61B 2017/00871; A61B 2017/0427; C08G 63/08; B29C 39/02

USPC ........ 606/76, 60, 232, 304; 623/23.56–23.63; 264/296
See application file for complete search history.

(56) References Cited

U.S. PATENT DOCUMENTS 4,950,258 A * 8/1990 Kawai ................ A61B 17/0644
264/230
5,705,181 A 1/1998 Cooper et al.
(Continued)

FOREIGN PATENT DOCUMENTS

EP 0326426 A2 8/1989
EP 1000958 A1 5/2000
(Continued)

OTHER PUBLICATIONS

Cotton et al, Composites of poly(DL-lactide-co-glycolide) and calcium carbonate: In vitro evaluation for use in orthopedic applications, Aug. 9, 2007, Wiley InterScience, pp. 195-205.*
(Continued)

*Primary Examiner* — Cris L Rodriguez
*Assistant Examiner* — Mirayda A Aponte
(74) *Attorney, Agent, or Firm* — Berggren Inc.

(57) ABSTRACT

A biodegradable medical device including at least one biodegradable material and having an initial shape and at least one evolved shape. The evolved shape is different from the initial shape. The initial shape is adapted to change towards the evolved shape due to an external stimulus. The medical device has a tension loaded to a predetermined tension level. The medical device is adapted to restore the tension to the predetermined tension level for at least 2 weeks in physiological conditions, or conditions simulating the physiological conditions.

9 Claims, 17 Drawing Sheets

Figure 1:
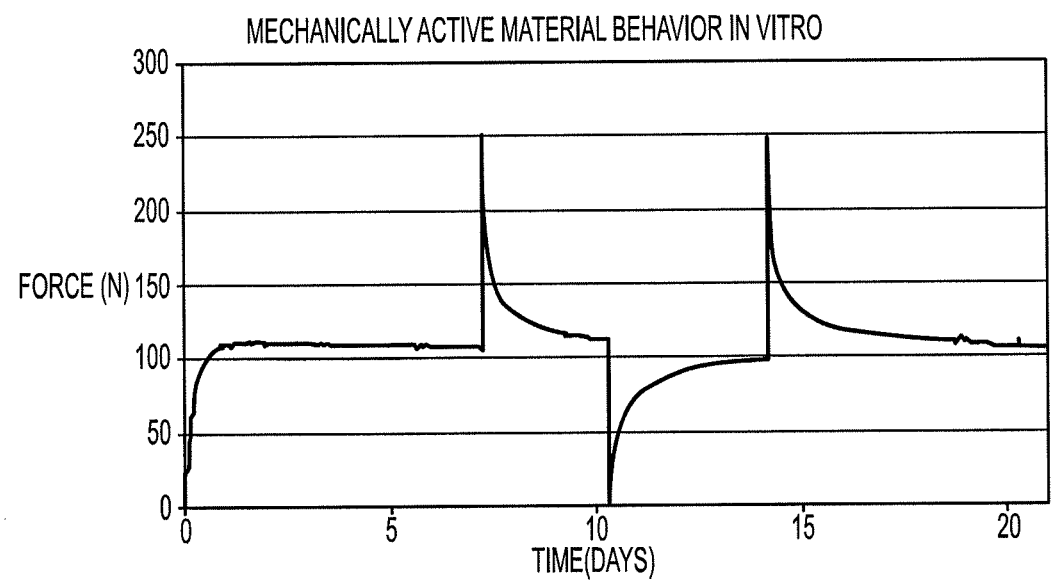

(51) Int. Cl.
  *A61L 31/06* (2006.01)
  *A61L 31/14* (2006.01)
  *A61B 17/66* (2006.01)
  *A61B 17/72* (2006.01)
  *A61B 17/00* (2006.01)
  *A61B 17/04* (2006.01)
  *C08G 63/08* (2006.01)

(52) U.S. Cl.
  CPC ............ *A61B2017/00867* (2013.01); *A61B 2017/00871* (2013.01); *A61B 2017/0427* (2013.01); *C08G 63/08* (2013.01)

(56) References Cited

U.S. PATENT DOCUMENTS

| | | | | |
|---|---|---|---|---|
| 6,605,090 B1* | 8/2003 | Trieu | ............... | A61B 17/8042 606/281 |
| 6,623,487 B1* | 9/2003 | Goshert | ............... | 606/329 |
| 2001/0004693 A1* | 6/2001 | Burkhead et al. | ............... | 606/73 |
| 2005/0033295 A1 | 2/2005 | Wisnewski | | |
| 2008/0234730 A1* | 9/2008 | Cotton | ............... | A61B 17/0401 606/232 |
| 2010/0318085 A1* | 12/2010 | Austin | ............... | A61B 17/0642 606/62 |

FOREIGN PATENT DOCUMENTS

| | | |
|---|---|---|
| EP | 1034806 A2 | 9/2000 |
| WO | WO-02/34310 A2 | 5/2002 |
| WO | WO-2006/092789 A2 | 9/2006 |
| WO | WO-2006/108114 A2 | 10/2006 |

OTHER PUBLICATIONS

Henna Niiranen et al.; In vitro and in vivo behavior of self-reinforced bioabsorbable polymer and self-reinforced bioabsorbable polymer/bioactive glass composites; 2004; pp. 699-708.

T. Niemela; Effect of β-tricalcium phosphate addition on the in vitro degradation of self-reinforced poly-L.D-lactide; Polymer Degradation and Stability 89; 2005; pp. 492-500.

M. E. Müller et al.; Manual of Internal Fixation, Techniques Recommended by the AP Group; 1979; 3 pages.

Harri Heino et al.; Influence of Self-Reinforcing on in Vitro Stress Relaxation of 70L/30D,L PLA; Conference abstract (oral presentation), 7th World Biomaterials Congress May 16-21, 2004, Sydney, Australia.

Non-English Finnish Search Report—Nov. 28, 2008.

Extended European Search Report, dated Mar. 3, 2010, issued in connection with counterpart Application No. 08105908.

* cited by examiner

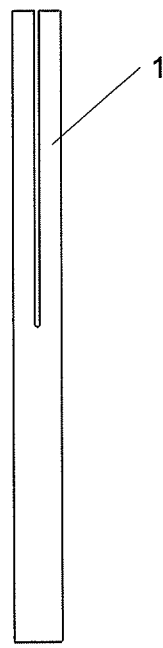 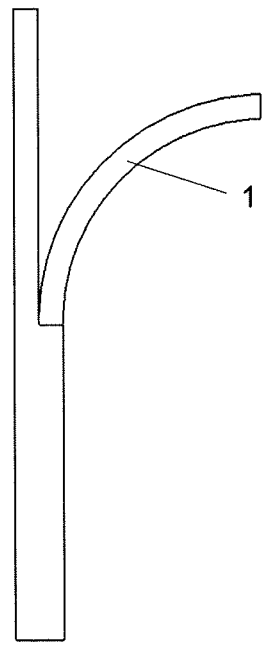
Fig. 3a　　　　　Fig. 3b
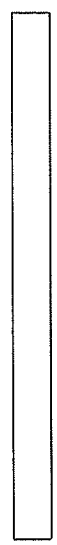 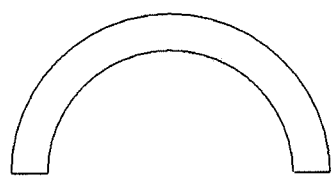
Fig. 4a　　Fig. 4b

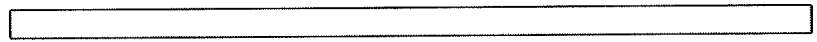
Fig. 5a
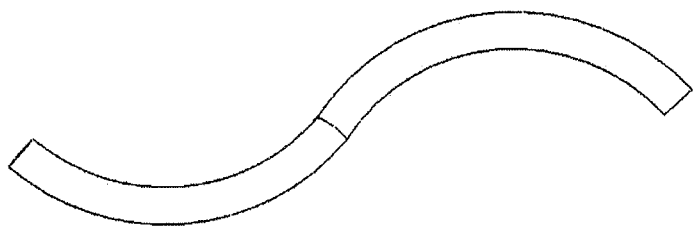
Fig. 5b
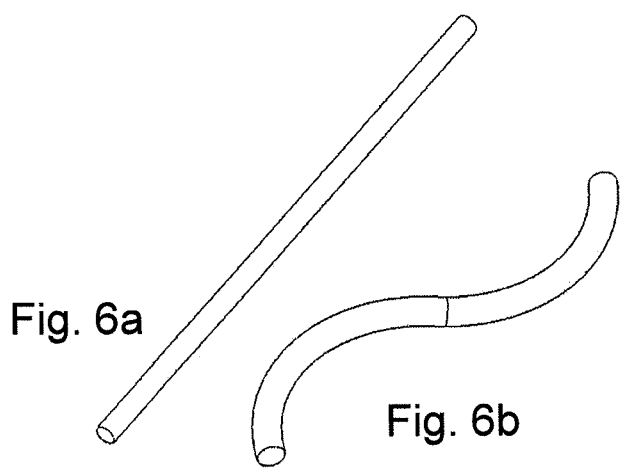
Fig. 6a
Fig. 6b

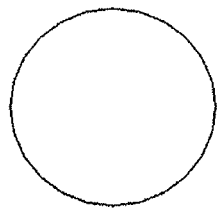
Fig. 7a
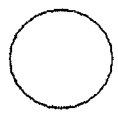
Fig. 7b
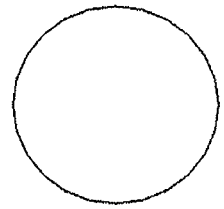
Fig. 7c
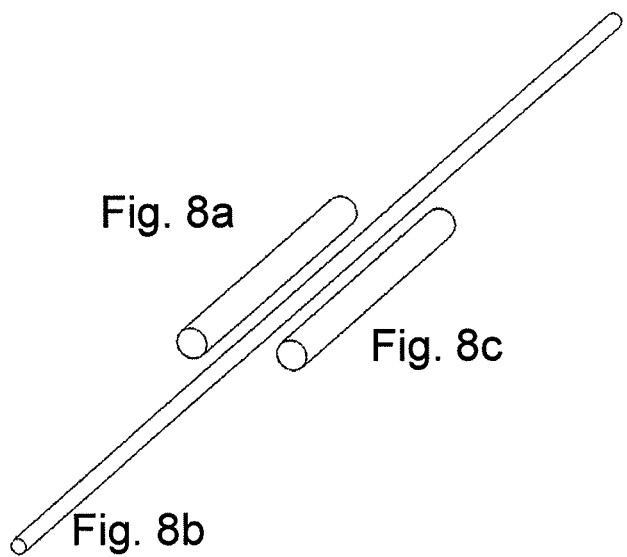
Fig. 8a
Fig. 8c
Fig. 8b

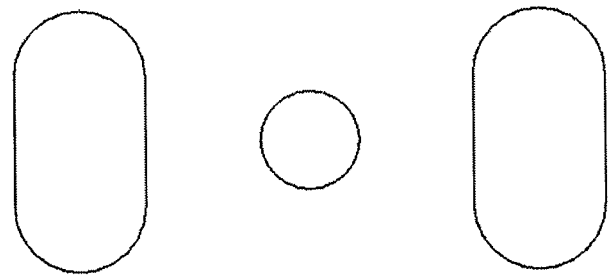
Fig. 9a    Fig. 9b    Fig. 9c
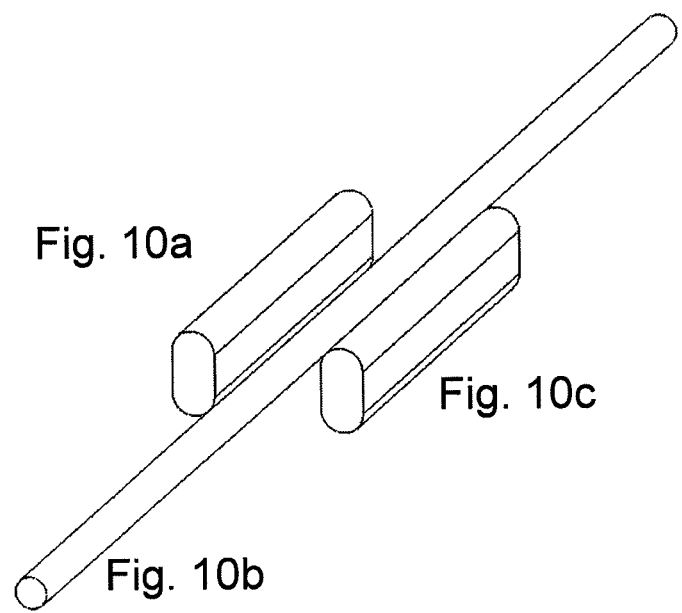
Fig. 10a
Fig. 10c
Fig. 10b

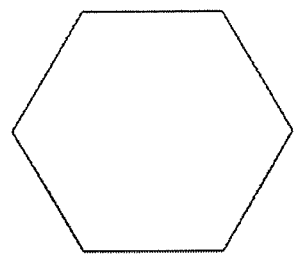
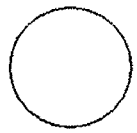
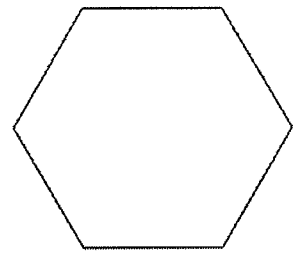
Fig. 11a       Fig. 11b       Fig. 11c
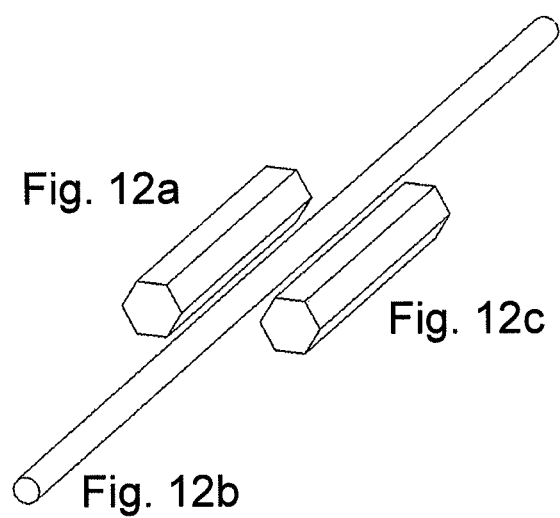
Fig. 12a
Fig. 12c
Fig. 12b

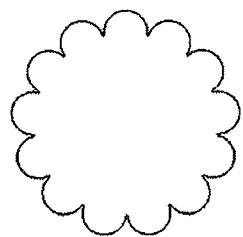 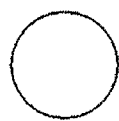 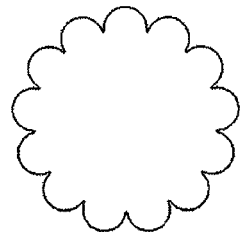
Fig. 13a  Fig. 13b  Fig. 13c
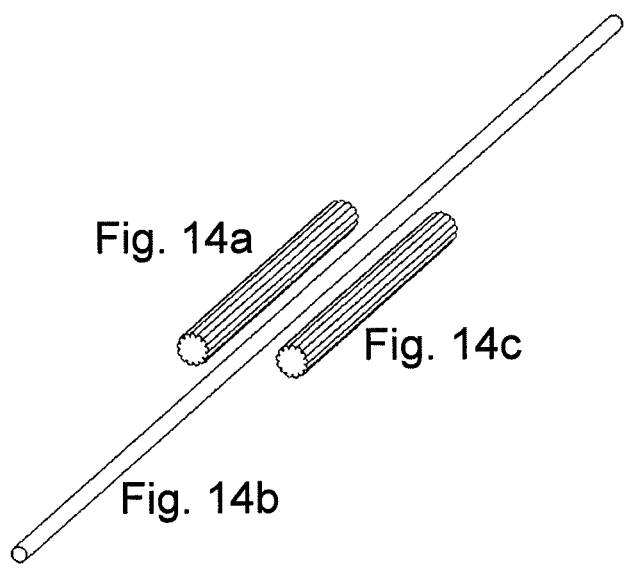
Fig. 14a
Fig. 14c
Fig. 14b

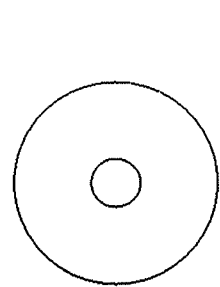
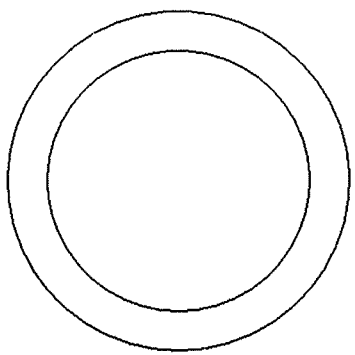
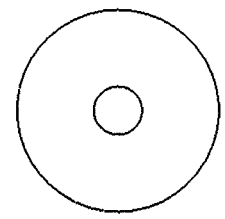
Fig. 15a    Fig. 15b    Fig. 15c
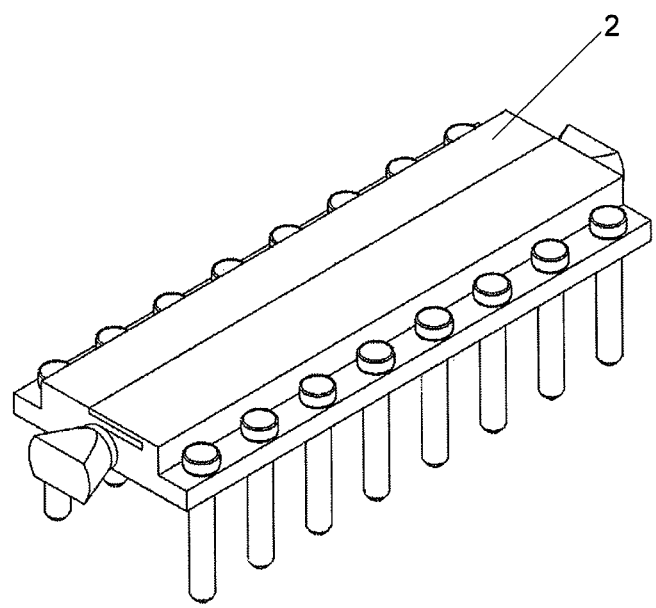
Fig. 16

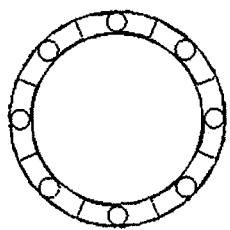
Fig. 25a
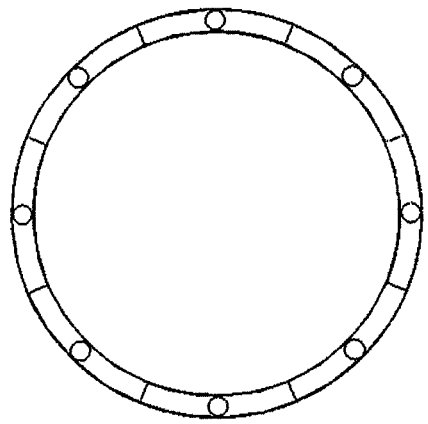
Fig. 25b
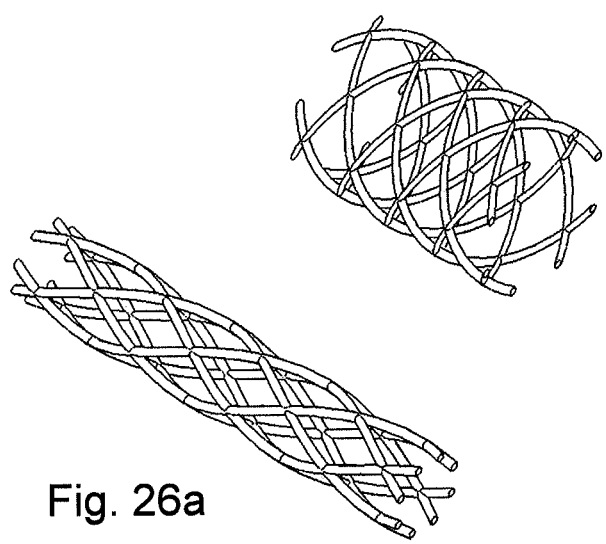
Fig. 26b
Fig. 26a

MEDICAL DEVICE AND ITS MANUFACTURE

CROSS-REFERENCE TO RELATED APPLICATIONS

This application claims priority to Finnish patent application 20075881 filed 5 Dec. 2007.

BACKGROUND

H. Heino, P. Törmälä, J. Ilomäki: "Influence of Self-Reinforcing on In Vitro Stress Relaxation of 70L/30D,L PLA", Conference abstract (oral presentation): $7^{th}$ World Biomaterials Congress 16-21 May 2004, Sydney, Australia, discloses not self-reinforced (not oriented) samples and self-reinforced (oriented) samples made 70L/30D,L PLA which were fixed to a sample holder and placed in phosphate buffer solution at 37° C. The self-reinforced samples tended to keep a certain level of stress after 7 days testing period, whereas the not oriented samples had no significant residual stress left after 1 day.

Publication US 2005/0033295 discloses implants formed of shape memory polymeric material for spinal fixation. The shape memory polymeric material may be biodegradable or non-biodegradable. The polymeric material tends to assume its memory condition by activation of a polymer transition. The activation can occur e.g. by adsorption of liquid by the polymer because the polymer may be formulated to be responsive to adsorption of a liquid by incorporating in the polymer a hydrophilic material.

SUMMARY OF THE INVENTION

The present invention provides a biodegradable medical device which has in physiological conditions the ability to undergo a dimensional change with a predetermined rate and extent, being at the same time able to exert predetermined forces on the healing tissues for a predetermined time, e.g. the medical device can exert compression on the healing tissues in the bone fracture or osteotomy fixation. For example, when a fixation is too tight or too loose, the medical device can restore the fixation tension to the predetermined level either by increasing the fixation tension due to the dimensional change, or by reducing the tension due to the stress relaxation of the material. The medical device is also adapted to change from its initial shape towards an evolved shape. When the medical device has an elongated structure, i.e. it is, for example, a screw, a pin, a tack or a nail, the medical device is able to increase its diameter and therefore the fixation strength between the medical device and the surrounding living material, e.g. bone, increases. The medical device can be activated by a stimulus of liquid in physiological conditions, or in conditions which simulate the physiological conditions. The molecules of the liquid reduce the energy level which is required for the dimensional change of the material. Due to the above-mentioned properties, the medical device is also insensitive to defects which may take place during a surgical operation or after it. Such defects can be, for example, the diameter of a drill hole in a bone may be too large, a surgeon may tighten a medical device too much, or parts of a fracture may move in respect of each other so that the tension in the device joining the parts of the fracture changes.

The importance of the compression in bone healing has been described, for example, in the Manual of Internal Fixation, Techniques recommended by AO-Group, 1979, p. 12. The international Association for the Study of Internal Fixation (AO/ASIF) has studied the effect of compression, and according to their studies, compression greatly enhances the stability of internal fixation. They also show that bone itself is able to maintain compression; thus, it is feasible to expect that the compression of the fixation device over the healing period can have a positive effect on bone healing.

Another example of an application offering benefit over the prior art made of the material of the present invention is a distraction osteogenesis device, bone distractor. Distractors are used to facilitate the modification of anatomy of bone structures by bone growth stimulated and guided by a movement created by a distractor device. The distractor device made using the technology of the present invention offers continuous movement with controlled rate, end point and force. Most often prior art distractors are operated manually, thus the movement is rather periodical than continuous. Manual operation requires access to the device, which always possess an increased infection risk.

DESCRIPTION OF THE INVENTION

The present invention relates to a biodegradable medical device which is made of at least one biodegradable material. The at least one biodegradable material may be selected from among homopolymers or copolymers. However, the medical device may be made of more than one biodegradable material. The biodegradable material may be a blend of two or more homopolymers or copolymers so that the blends may comprise only homopolymers, only copolymers, or at least one homopolymer and at least one copolymer. The material may also be made of at least one polymeric component, such as a homopolymer or copolymer, and at least one auxiliary agent. The auxiliary agent may consist, for example, of monomers or a hydrophilic component. The medical device may also comprise mechanically active and non-active components, each one of them made of biodegradable material.

The biodegradable polymeric materials may be selected, for example, from among the following materials: polyglycolide (PGA), copolymers of glycolide, polylactides, copolymers of polylactide, unsymmetrically 3,6-substituted poly-1,4-dioxane-2,5 diones, poly-•-hydroxybutyrate (PHBA), PHBA/•-hydroxyvalerate copolymers (PHBA/HVA), poly-•-hydroxypropionate (PHPA), poly-p-dioxanone (PDS), poly-•-valerolactone, poly-•-caprolactone, methyl methacrylate-N-vinyl pyrrolidine copolymers, polyesteramides, polyesters of oxalic acid, polydihydropyrans, polyalkyl-2-cyanoacrylates, polyurethanes (PU), polyvinylalcohol (PVA), polypeptides, poly-•-malic acid (PMLA), poly-•-alkanoic acids, polyethyleneoxide (PEO) and chitine polymers. Copolymers of glycolide comprise, for example, glycolide/L-lactide copolymers (PGA/PLLA) and glycolide/trimethylene carbonate copolymers (PGA/TMC). Polylactides comprise, for example, poly-L-lactide (PLLA), poly-D-lactide (PDLA) and poly-DL-lactide (PDLLA). Copolymers of polylactide comprise, for example, L-lactide/DL-lactide copolymers, L-lactide/D-lactide copolymers, lactide/tetramethylglycolide copolymers, lactide/trimethylene carbonate copolymers, lactide/•-valerolactone copolymer, lactide/•-caprolactone copolymer, polydepsipeptides (glycine-DL-lactide copolymer), polylactide/polyethylene oxide copolymers, glycolide/L-lactide (PGA/PLLA)/polyethylene glycol (PEG) copolymers and polylactide/polyethylene glycol (PEG) copolymers.

The medical device may also be reinforced by reinforcing the material by using fibres manufactured of a resorbable polymer or of a polymer alloy, or with biodegradable ceramic fibres, such as •-tricalciumphosphate fibres or bioactive glass fibres. Ceramic powders can also be used as additives or fillers in the medical device to promote new bone formation.

Further, the medical device may comprise various biocompatible additives for facilitating the processability of the material (e.g. stabilizers, antioxidants or plasticizers) or for changing its properties (e.g. plasticizers or ceramic powder materials or biostable fibers, such as carbon) or for facilitating its treatment (e.g. colorants).

The medical device may also contain some other bioactive additive(s), such as antibiotic(s) or other drug(s), chemotherapeutic agents, agents activating the healing of wounds, growth factor(s), bone morphogenic protein(s), anticoagulant (such as heparin) etc. Such bioactive medical devices are particularly advantageous in clinical use, because they have, in addition to their mechanical effect, also biochemical, medical and other effects to facilitate tissue healing and/or regeneration.

The medical device has an initial shape and at least one evolved shape. The evolved shape is different from the initial shape. The initial shape is adapted to change towards the evolved shape in physiological conditions, physiological conditions meaning aqueous environment and temperature at the range of 35° C. to 42° C. In other words, the initial shape is the shape which the medical device has after it has been manufactured, and the evolved shape is the shape towards which the shape of the medical device changes when the medical device is activated in physiological or similar conditions. Thus, the shape-changing behavior of the medical device can also be observed outside the bodily conditions. It should be noted that the change from the initial shape to the evolved shape does not take place in dry conditions but the phenomenon requires the stimulus of the liquid in physiological conditions, or in conditions simulating the physiological conditions.

The medical device can be manufactured so that it has a predetermined speed to change towards the evolved shape. The biodegradable medical device is also programmed to change towards the evolved shape but it does not necessarily reach the evolved shape but there is a predetermined shape between the initial shape and the evolved shape until which the medical device changes towards the evolved shape.

The dimensional change which takes place during the change from the initial shape towards the evolved shape is more than 2% but it is often equal to or greater than 5%. For example, the diameter of an elongated medical device, such as a nail, screw, pin or tack, may increase so that its diameter is more than 2% and in the preferred case more than 5% larger than in its initial shape.

The medical device is also loaded to have a predetermined tension. The method how the medical device may be loaded with the predetermined tension will be explained below. The medical device is adapted to restore its tension to the predetermined tension level for at least 2 weeks under physiological conditions, i.e. for at least 2 weeks after implantation or for at least two weeks in a simulated body fluid at a temperature of 37° C. The simulated body fluid is a phosphate buffer solution or other liquid simulating the conditions of human tissues. In order to observe this tension-restoring ability of the medical device in vitro, the medical device must be rigidly fixed (locked) in its place and it must be immersed in a liquid at physiological temperature. It should be noted that the medical device is adapted to restore its tension regardless of external loads exerted on it provided that the loads are reasonable in regard to the load carrying capacity of the medical device.

Due to the predetermined tension which has been loaded in the medical device, the medical device tends to restore its tension to the predetermined tension level. When the tension of the medical device is below the predetermined tension, the medical device contracts and restores the predetermined tension. This may happen, for example, when the fixation is too loose. The speed of contraction can also be adjusted in advance during the manufacture of the medical device. When the tension of the medical device is above the predetermined tension, the medical device reduces the tension through a controlled stress relaxation so that the predetermined tension is achieved. This may happen, for instance, when a surgeon has tightened the medical device over the predetermined tension.

As one can readily understand, the time range during which the medical device is able to restore its tension level is adjustable. The time range should be adjusted so that it is sensible in respect of the healing period of an injury. It is natural that the ability to restore the predetermined tension weakens when the medical device has achieved a certain point in degrading. However, periods that are significant in regard to the healing of the injury are easily achievable. For example, two weeks may be an adequate period for the initial consolidation of a bone fracture or a growth plate fracture of a small baby, but four to six weeks may be required to achieve the consolidation of cancellous bone fracture in the case of adults.

The method of the invention for manufacturing a biodegradable medical device starts by the selection of at least one biodegradable material. After the material selection, a preform is formed via melt processing of at least one biodegradable material. In the melt processing step, granular raw materials are molten, mixed and subsequently given the desired form. The preferred methods for forming the preform are extrusion, injection moulding and compression moulding. The extrusion process yields a continuous preform profile, whereas the injection moulding and compression moulding can be used to manufacture preform parts. Twin screw extrusion is a preferable melt processing method due to its mixing efficiency, which enables the production of good quality preforms with one or more auxiliary components. Depending on the raw materials, the processing temperatures in the melt processing may vary between 50° C. and 300° C.

After the melt processing, the preform possesses a non-oriented original shape. A deformation process follows the melt processing step. The deformation process actually creates the mechanical activity properties of the material. In the deformation process, the preform is deformed at a temperature which is adequate to cause a temporary change in its shape so that the deformed preform achieves the initial shape of the medical device. The deformation process may be, for example, die drawing, free drawing, twisting, ring enlargement, compression, or bending. Practically any deformation made in the material can be recovered as mechanical activity in physiological conditions. The deformation takes place at a temperature which is above the glass transition temperature and below the melting temperature of the material. The direction and the maximal extent of movement are defined in this processing step. In practice, the theoretical maximum mechanical activity movement is equal to the deformation applied in this processing step.

In the deformation process, the preform is loaded with a predetermined tension. The level of the predetermined tension depends on the temperature and the deformation ratio, e.g. the draw ratio. The predetermined tension, i.e. the force level, is adjusted in the deformation process by changing the deformation temperature. At low temperatures, high forces are required to create the deformation, and therefore, the medical device is able to produce high forces when it is in use in physiological conditions or conditions simulating the physiological conditions. At high temperatures, only low forces are required to cause the deformation and therefore, the medical device is able to produce only low forces in use in physiological conditions or conditions simulating the physiological conditions.

In the following step, the deformed preform is cooled while still maintaining the predetermined level of stress, and the initial shape and the predetermined tension is fixed. In order to create certain features in the medical device, a finishing step may be required. However, the finishing step may be omitted. The finishing step may include at least one of machining or thermoforming. In the finishing step after the deformation, care must be taken to preserve the mechanical activity in the desired areas. For example, thermoforming of the head for a contraction nail removes the mechanical activity properties of the head due to the deformation towards the direction in which the mechanical activity would drive the material. This is, however, beneficial in this case, because the head of the nail is preferably dimensionally stable and the activity comes from the shaft. Mechanical activity properties can also be modified by treating the material thermally or mechanically after the deformation process. A tubular rod which would decrease in length and increase in diameter can e.g. be thermally treated on one side to partially release the stresses created in the deformation process, whereby a rod is created which will curve strongly when the mechanical activity properties are activated. A similar effect can be achieved with asymmetrical machining of the material. Finally, the ready-made medical device is sterilized, for example, by gamma irradiation.

The raw material selection defines a frame for the strength and for the strength retention time but also sets some limits on the mechanical activity. The properties of the medical device are mainly adjusted by the raw material selection and the manufacturing method. As stated before, there is a vast selection of raw materials available. By selecting the raw materials and determining their amounts, it is possible to obtain the desired properties for the medical device. As also stated before, the material selection can be made from among homopolymers, copolymers, or blends. A polymeric component or polymeric components may be accompanied by at least one auxiliary agent. The auxiliary agent may consist of monomers. The monomers may be fed, for example, into an extruder and mixed with the polymeric component. However, the monomer can also be generated in the material by increasing the processing temperature to a level which enables spontaneous monomer generation through thermal degradation of the polymer. For example, a copolymer of glycolide and lactide may have an L-lactide monomer as an auxiliary agent.

The biodegradable medical device may also consist of a copolymer of D-lactide and L-lactide. The copolymer of D-lactide and L-lactide may comprise D-lactide from 98 wt.-% to 2 wt.-%, and L-lactide from 2 wt.-% to 98 wt.-%. For example, the material may be PLA 50D/50L.

The biodegradable medical device may also comprise a copolymer of L-lactide and DL-lactide. The copolymer of L-lactide and DL-lactide may comprise L-lactide from 96 wt.-% to 4 wt.-% and DL-lactide from 4 wt.-% to 96 wt.-%. For example, the material may be PLA 70L/30DL. In addition to the copolymer of L-lactide and DL-lactide, the medical device may comprise L-lactide monomers. Their content may range from 0.1 wt.-% to 10 wt.-%.

The biodegradable medical device may also comprise a blend of a copolymer of lactide and glycolide and a copolymer of D-lactide and L-lactide. The copolymer of lactide and glycolide may comprise from 5 wt.-% to 95 wt.-% of lactide and from 95 wt.-% to 5 wt.-% of glycolide. The copolymer of D-lactide and L-lactide may comprise from 98 wt.-% to 2 wt.-% of D-lactide and from 2 wt.-% to 98 wt.-% of L-lactide.

DETAILED DESCRIPTION OF THE INVENTION

Figures 2A, 2B:
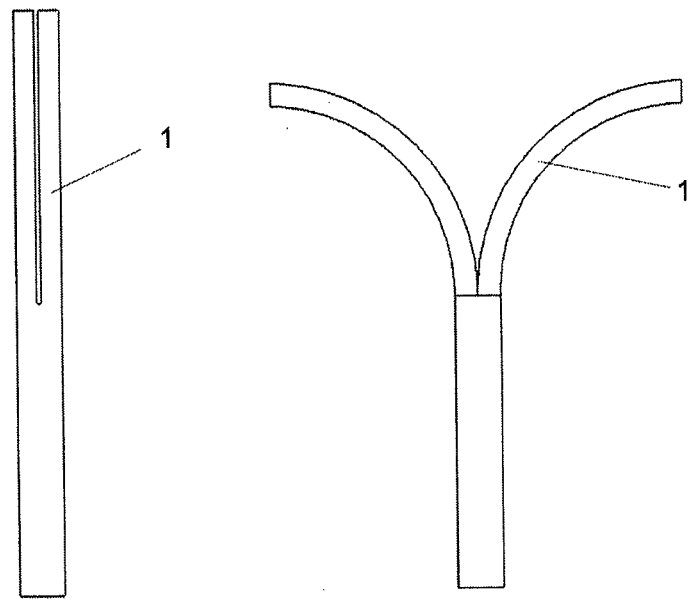
Figure 17:
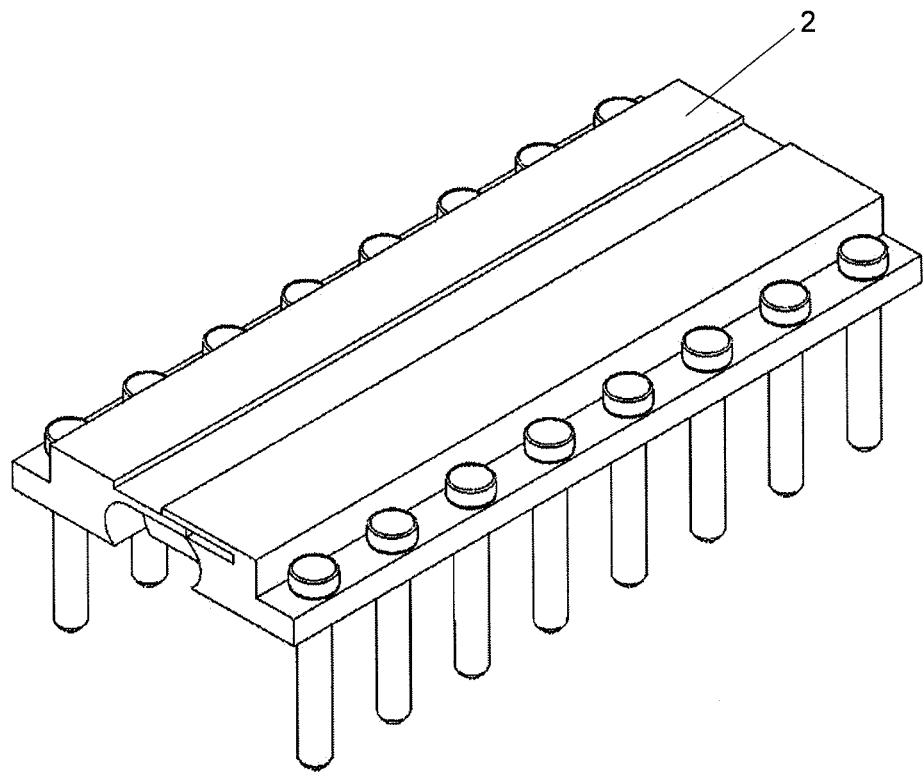
Figure 18:
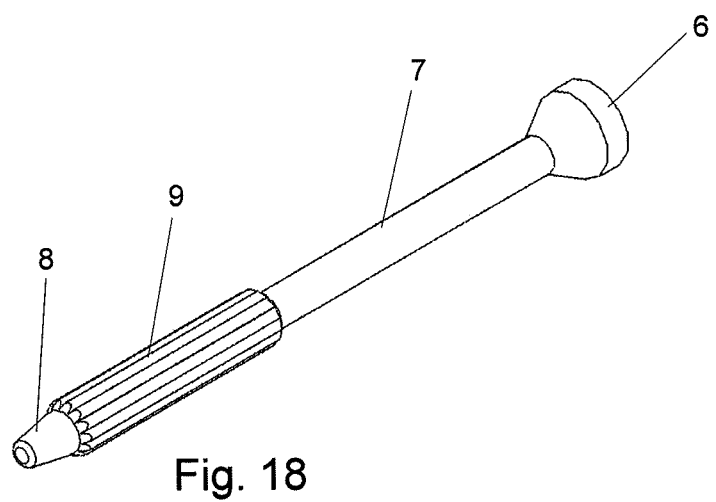
Figure 19:
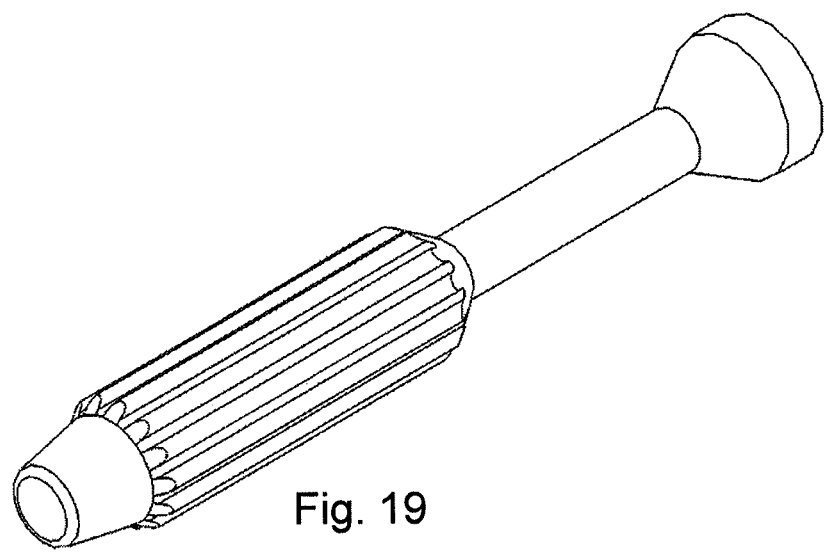
Figure 20:
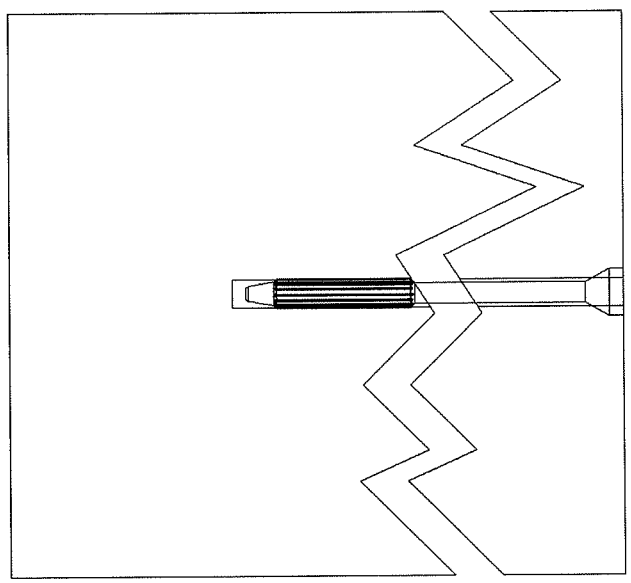
Figure 21:
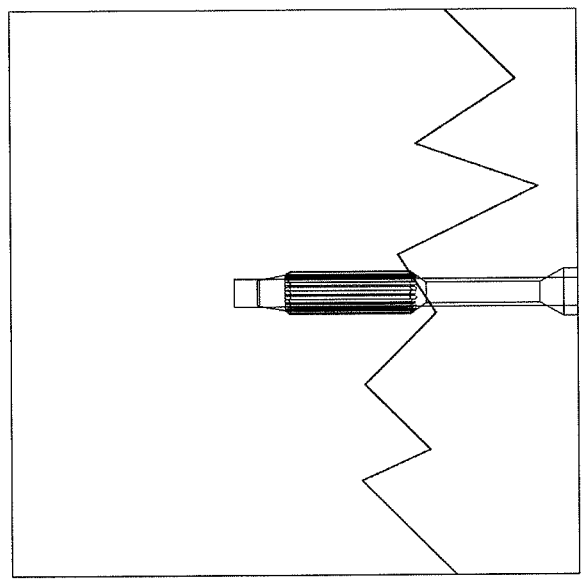
Figure 22A:
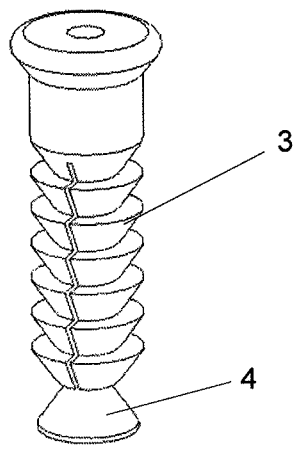
Figure 22B:
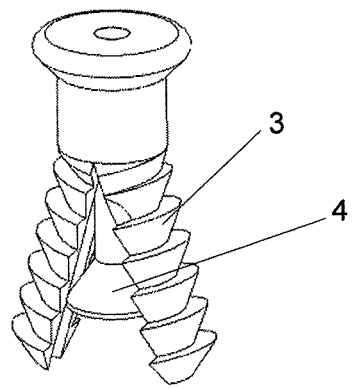
Figures 23A, 23B, 23C:
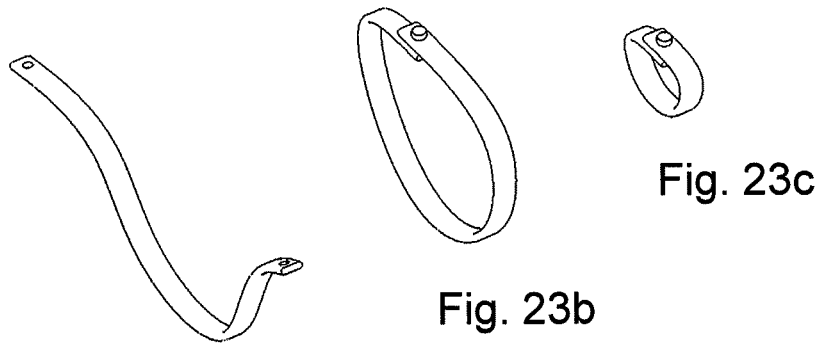
Figures 24A, 24B:
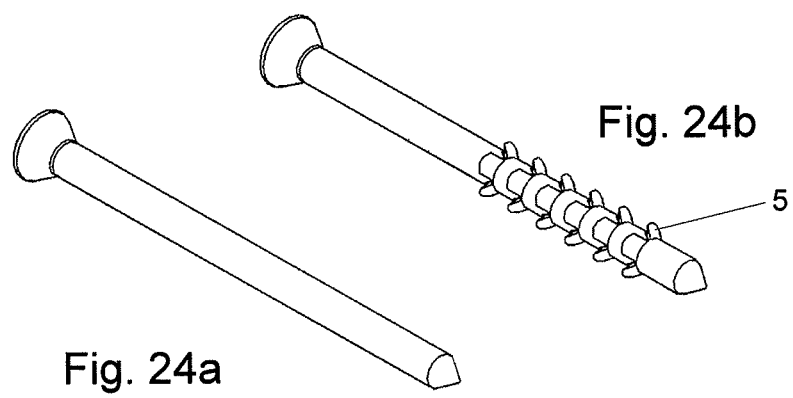
Figure 27A:
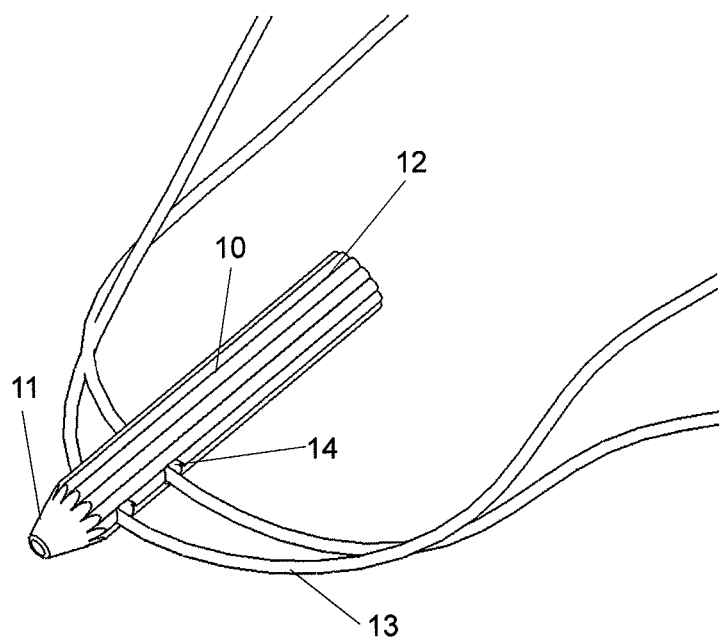
Figure 27B:
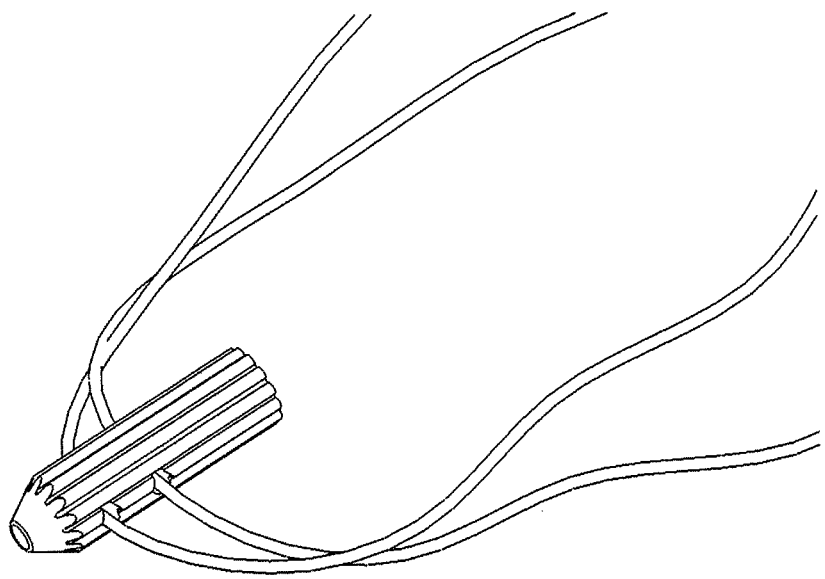
Figure 28:
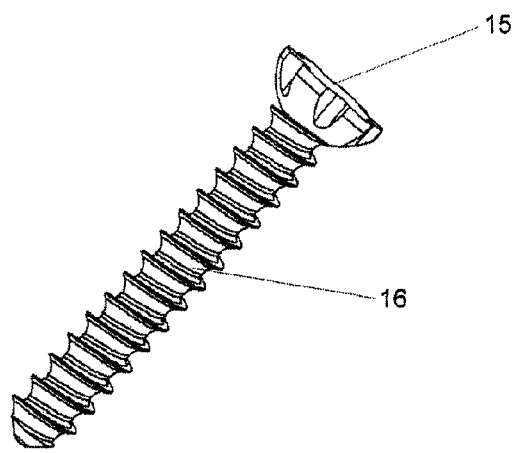
Figure 29:
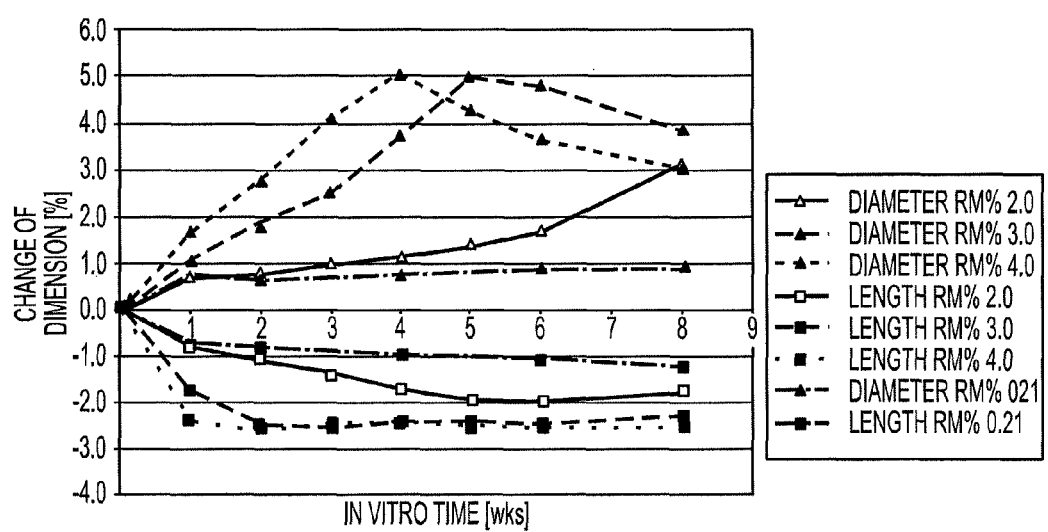
Figure 30:
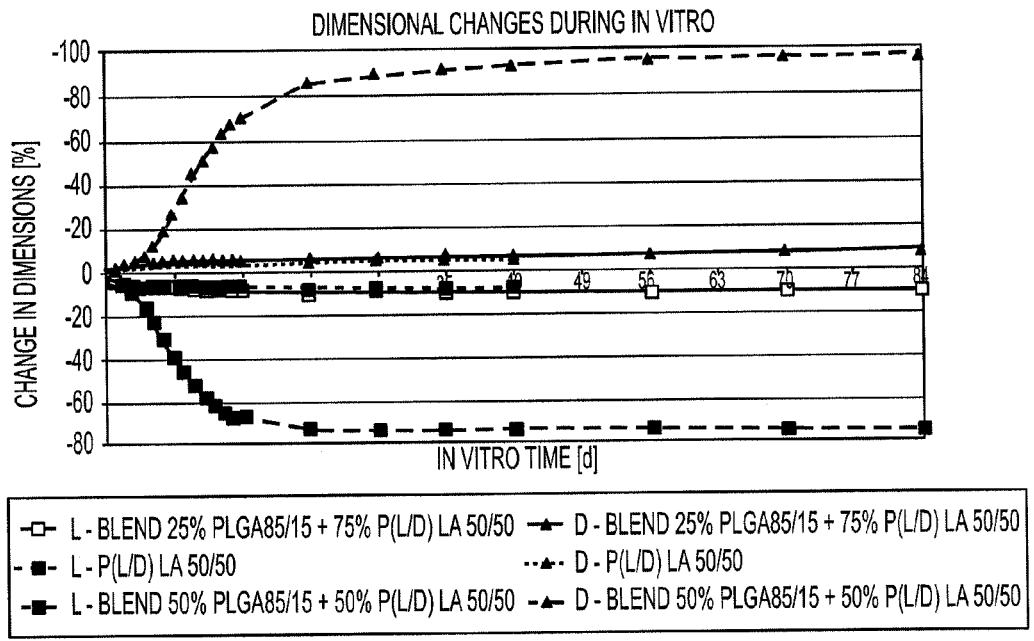
Figure 31:
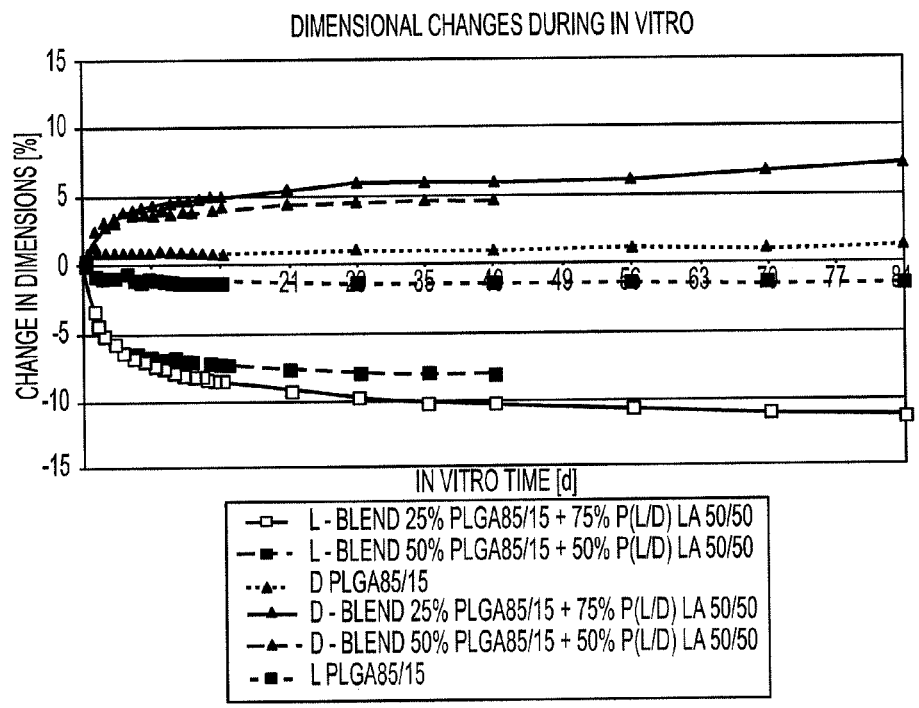
Figure 32:
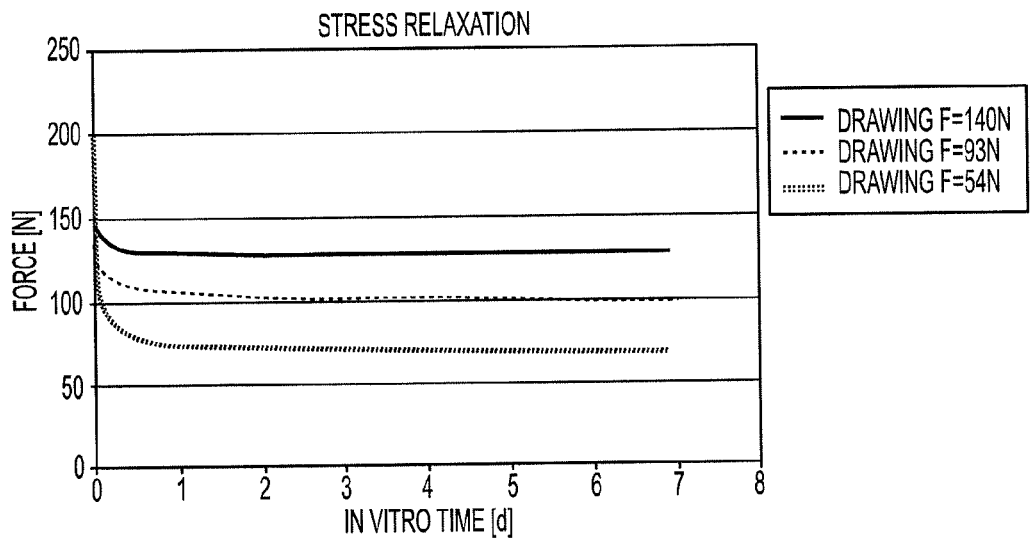
Figure 33:
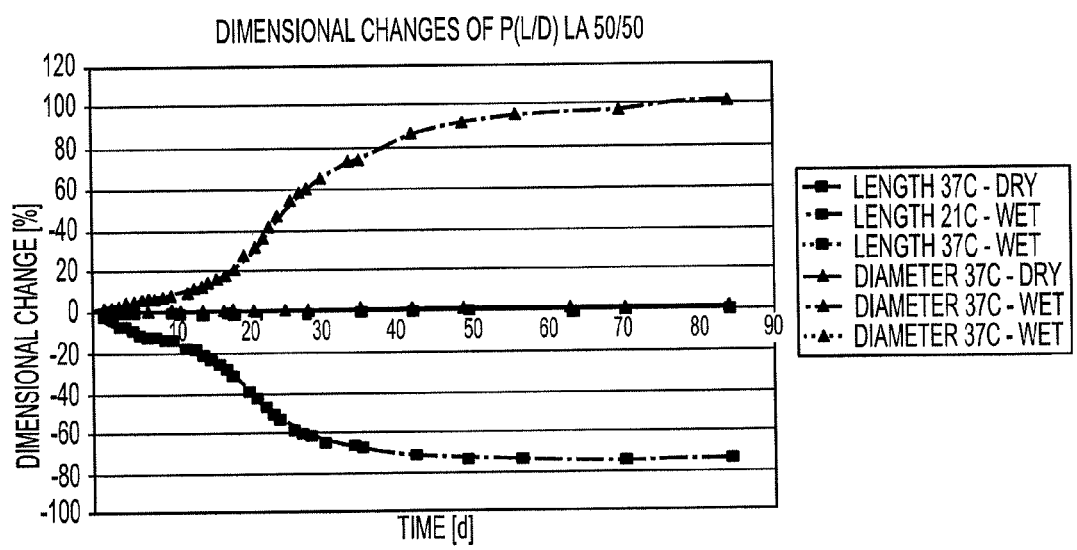

In the following, the invention will be described by referring to the appended drawings in which FIG. 1 shows a diagram on combined stress relaxation and force generation test data for a mechanically active material according to the present invention, FIGS. 2a and 2b show a preform of a medical device in which the mechanical shape memory is programmed to open a closed fork, FIGS. 3a and 3b show a preform of a medical device in which the mechanical shape memory is programmed to bend one of the two halves of a fork, FIGS. 4a and 4b show a preform of a medical device in which the mechanical shape memory is programmed to bend the initial rod or other shape according to predefined programming, FIGS. 5a and 5b show a preform of a medical device in which the mechanical shape memory is programmed to bend the initial rod or other shape according to predefined programming, FIGS. 6a and 6b show a preform of a medical device in which the mechanical shape memory is programmed to bend the initial rod or other shape according to predefined programming, FIGS. 7a, 7b and 7c show the cross-section of a preform of a medical device, FIGS. 8a, 8b and 8c show a perspective view of the preform of the medical device of FIG. 7, FIGS. 9a, 9b and 9c show the cross-section of a preform of a medical device, FIGS. 10a, 10b and 10c show a perspective view of the preform of the medical device of FIG. 9, FIGS. 11a, 11b and 11c show the cross-section of a preform of a medical device, FIGS. 12a, 12b and 12c show a perspective view of the preform of the medical device of FIGS. 11a, 11b and 11c, FIGS. 13a, 13b and 13c show the cross-section of a preform of a medical device, FIGS. 14a, 14b and 14c show a perspective view of a preform of a medical device, FIGS. 15a, 15b and 15c show the cross-section of a preform of a medical device, FIGS. 16 and 17 show a perspective view of a medical device for distraction osteogenesis, FIGS. 18 and 19 show a perspective view of a medical device for bone fracture fixation, FIGS. 20 and 21 show a schematic view of a medical device when it is used for bone fracture fixation, FIGS. 22a and 22b show a perspective view of a medical device; in this case the medical device is a medical fastener, FIGS. 23a, 23b and 23c shows a perspective view of a medical device; in this case the medical device is a fastening band, FIGS. 24a and 24b shows a perspective view of a medical device for fracture fixation of soft tissue fixation to the bone, FIGS. 25a and 25b show the cross-section of a medical device, FIGS. 26a and 26b show a perspective view of the medical device of FIGS. 25a and 25b, FIGS. 27a and 27b show a perspective view of a medical device, FIG. 28 shows a perspective view of a medical device, in this case a screw, FIG. 29 shows a diagram on the effect of L-lactide monomer (auxiliary component) content on the dimensional changes in physiological conditions, FIG. 30 shows a diagram on the effect of blending of dimensionally stable and dimensionally unstable polymers on the dimensional changes in physiological conditions, FIG. 31 shows a diagram on the dimensional changes of PLA 50L/50D and PLGA 85L/15G blends, FIG. 32 shows a diagram on the effect of the deformation force on the residual force in stress relaxation testing, and FIG. 33 shows dimensional changes of P(L/D)LA 50/50 in 37° C. dry environment and in 21° C. and 37° C. aqueous environment.

THE MATERIAL PROPERTIES

The material of the present invention shows controllable mechanical activity properties. The material has the ability to contract at a predetermined contraction speed to a predetermined extent, being able to produce a predetermined force in a predetermined direction. On the other hand, when excess stress is applied to the material, the material reduces the stress due to the controlled stress relaxation to a predetermined level. The FIG. 1 shows a diagram on the test results of a combined stress relaxation and contraction test.

The predetermined tension of the medical device was adjusted to be 100 N.

The test is made by first attaching a 3 mm thick rod at both ends in the test system. The test is carried out in a phosphate buffer solution at 37° C. The composition of the buffer solution is: 0.0546 mol/l of $Na_2HPO_4$ and 0.0121 mol/l of $KH_2PO_4$. The pH of the solution is 7.4±0.2. The contraction force which the sample is able to generate is measured, but no contraction is allowed. The sample gradually generates a force of about 100 N. In the next step, the sample is mechanically stressed up to 250 N and the system is locked in position. The sample starts to gradually decrease the stress down to slightly above 100 N, although no contraction of the sample is allowed. The sample tends to keep this achieved stress level. The stress of the sample is again mechanically relieved and the position is locked. The sample is again capable of generating a force of about 100 N in the test system. One more tensioning to 250 N yields similar gradual decrease down to 100 N as noted previously. In a summary, the stress level is programmed to the material and it tends to keep it in spite of the disturbances from the environment.

In general, the above described test method may be used to test the medical device in regard to its ability to maintain the predetermined tension level.

The Medical Device Solutions

There are various ways to utilize the mechanical activity in bioabsorbable medical devices. Some examples of medical devices based on mechanically active shape memory polymers are presented below.

FIGS. 2a and 2b show a preform of a medical device in which the mechanical shape memory is programmed to open a closed fork. FIG. 2a shows the preform of the medical device in its initial condition and FIG. 2b shows the preform of the medical device when it has been changed towards the evolved shape.

The mechanical shape memory is based on the fact that the oriented and stressed polymer chains contract towards the initial non-oriented state. When the orientation is removed from the inner side of the fork spikes 1, the oriented and stressed polymer chains contract towards the original non-oriented state thus the sides of the fork tend to bend outwards. The bending will continue until the stress between the inner and the outer side of the fork spikes 1 are in the same level of stress or until an external stress exerted on the article is as great as the stress generated by the contracting polymer chains. The degree of bending can be adjusted by adjusting the temperature and time, which are to deorient the selected parts of the preform.

FIGS. 3a and 3b show a preform of a medical device in which the mechanical shape memory is programmed to bend one of the two halves of a fork. FIG. 3a shows the preform of the medical device in its initial condition and FIG. 3b shows the preform of the medical device when it has been changed towards the evolved shape.

When the orientation is removed from the inner side of one of the fork spikes 1, the oriented and stressed polymer chains contract towards the initial non-oriented state; thus, the spike of the fork is bent. The bending will continue until the stress between the inner and the outer sides of the fork spikes 1 are in the same level of stress or until an external stress exerted on the article is as great as the stress generated by the contracting polymer chains. Spikes 1 which are not thermally treated will not tend to bend due to the homogeneity of the internal stress of the polymer spike.

FIGS. 4a and 4b show a preform of a medical device in which the mechanical shape memory is programmed to bend the initial rod or other shape according to predefined programming. FIG. 4a shows the preform of the medical device in its initial condition and FIG. 4b shows the preform of the medical device when it has been changed towards the evolved shape.

The programming is based on the controlled removal of the oriented polymer structure. The rod or other shape will tend to bend to the opposite side from which the orientation has been removed. The degree of shape change can be adjusted according to thermal treatment of the polymer article or by controlling the oriented polymer structure itself.

FIGS. 5a, 5b, 6a and 6b show a preform of a medical device in which the mechanical shape memory is programmed to bend the initial rod or other shape according to predefined programming. FIGS. 5a and 6a show the preform of the medical device in its initial condition, and FIGS. 5b and 6b show the preform of the medical device when it has been changed towards the evolved shape. The thermal treatment is performed on opposite sides of the halves of the rod. Thus the shape tends to shift towards the S-shape.

FIGS. 7a, 7b and 7c show the cross-section of a preform of a medical device and FIGS. 8a, 8b and 8c show a perspective view of the preform of the medical device of FIG. 7. The medical device in these drawings is a preform of a medical device in which the mechanical shape memory is programmed to deform from a spherical temporary shape to a spherical permanent shape. The shape change is due to the mechanical activity of the material which has been oriented for example in a die drawing process. The original and permanent shape, which is shown is FIGS. 7a and 8a, is due to the melt processing of the polymer. The polymer structure after melt processing is non-oriented. After the die drawing, the polymer structure is oriented (see FIGS. 7b and 8b) and this enables the dimensional change towards the evolved and permanent structure, which is shown in FIGS. 7c and 8c. As one can see from FIGS. 7a, 8a, 7c and 8c, the original shape of the preform of the medical device corresponds to the evolved shape of the preform of medical device. The diameter of the article expands as the length of the article shortens. The contraction-expansion behavior can be adjusted by the degree of the orientation.

FIGS. 9a, 9b and 9c show the cross-section of a preform of a medical device, FIGS. 10a, 10b and 10c show a perspective view of the preform of the medical device of FIG. 9. The preform of the medical device in these drawings is a preform of a medical device in which the mechanical shape memory is programmed to deform from a spherical temporary shape to an ellipsoidal permanent shape. As in above mentioned example, the original and permanent shape is in non-oriented state. The article tends to change its shape towards the evolved and permanent shape which is the ellipsoidal shape.

FIGS. 11a, 11b and 11c show the cross-section of a preform of a medical device, FIGS. 12a, 12b and 12c show a perspective view of the preform of a medical device of FIGS. 11a, 11b and 11c. The preform of the medical device in these drawings is a preform of a medical device in which the mechanical shape memory is programmed to deform from a spherical temporary shape to an angular permanent shape. As in the above mentioned example, the original and permanent shape is in non-oriented state. The article tends to change its shape towards the evolved and permanent shape which is the angular shape, and which corresponds to the original permanent shape.

FIGS. 13a, 13b and 13c show the cross-section of a preform of a medical device, FIGS. 14a, 14b and 14c show a perspective view of a preform of a medical device. The preform of the medical device in these drawings is a preform of a medical device in which the mechanical shape memory is programmed to deform from a spherical temporary shape to a grooved spherical permanent shape. As in the above mentioned examples, the original and permanent shape is in non-oriented state. The article tends to change its shape towards the evolved and permanent shape which is the grooved spherical shape and corresponds to the original permanent shape.

The preform of the medical device may be useful in the manufacture of a bioabsorbable, sterilizable polymeric or composite bone fracture or osteotomy fixation device, such as a pin comprising a shaft. The surface of the shaft is smooth in its initial state but comprises longitudinal grooves in its evolved state. Between the grooves there are naturally ridges. The fixation device can also be a bioabsorbable tack (a pin with a widening head) comprising a shaft. The surface of the shaft is also provided with longitudinal grooves and ridges in its evolved state. The fixation device may comprise a copolymer of L-lactide and glycolide, the content of L-lactide ranging from 5 wt.-% to 95 wt.-% and the amount of glycolide ranging from 95 wt.-% to 5 wt.-%. The fixation device may comprise L-lactide monomers as an auxiliary agent. The content of L-lactide monomers may vary between 0.1 wt.-% and 4 wt.-%. The predetermined tension of the medical device may vary between e.g. 5 N and 250 N. For example, the pins having the predetermined tension of 100 N are useful in the fixation of cancellous bone fractures of foot and hand.

FIGS. 15a, 15b and 15c show the cross-section of a preform of a medical device. The medical device in these drawings is a medical device in which the mechanical shape memory is programmed to deform from a ring or a tubular temporary shape to a ring or a tubular permanent shape. As in the above mentioned examples, the original and permanent shape is in non-oriented state. The article tends to deform towards the evolved and permanent shape which corresponds to the original permanent shape.

FIGS. 16 and 17 show a perspective view of a medical device for distraction osteogenesis. The distraction device comprises dimensionally stabile frame structure and a mechanically active element 2. The mechanically active shape memory element of the distraction device generates an expulsive force on the dimensionally stable frame. As the mechanically active shape memory element contracts, the contraction force is converted to an expulsive force on the frame structure. As the frame structure is fastened to bone tissue, the force generated by the mechanically active element is transmitted to the bone tissue. The extrinsic force transmitted to the bone tissue enforces the bone tissue to grow in the direction of the applied force. The distraction device can be composed of one or multiple contracting or expanding elements which enable the movement of the fastened edges of the device.

FIGS. 18 and 19 show a perspective view of a medical device for bone fracture fixation. The mechanically active shape memory device is comprised of a grooved head which enables the tight initial fixation in the bone tissue and a contracting shaft which generates a predefined compression on the fracture site. The grooved part of the device tends to expand as the whole device tends to contract according to the predefined material programming.

FIGS. 20 and 21 show a schematic view of a medical device when it is used for bone fracture fixation. In these drawings, the medical device is an orthopedic nail for bone fracture fixation. The orthopedic nail comprises a head 6, an elongated shaft 7 and a tapering tip 8. On the shaft 7 there is a length which comprises ridges 9 and, naturally, grooves therebetween. The head 6 comprises a recess (not shown) for an implanting tool. The shape change is shown in FIGS. 18 and 19. The initial mechanism of locking to bone is achieved by the grooved shape near the tip of the nail. The attachment to the bone is enhanced by the dimensional change of the device. The oriented structure of the medical device tends to contract, and at the same time, the diameter of the round device tends to expand, thus enhancing the fixation to the bone. On the other hand, the contraction, which occurs on the longitudinal axis of the device, pulls the fixed bone fragments together and thus tightens the fixation of the fracture site. As shown in FIG. 1, the device is also capable of adjusting the stress level of the fracture surface to a predefined level if the manual fixation is too tight or too loose.

FIGS. 22a and 22b show a perspective view of a medical device; in this case the medical device is a medical fastener. The medical fastener comprises a dimensionally stable body 3 and a mechanically active shape memory element 4. The grip of the fastener is tightened as the mechanically active shape memory element contracts and opens the structure. The edges of the body are compressed against the walls of the drill hole, thus enabling a tighter fastening over time.

FIG. 23 shows a perspective view of a medical device; in this case the medical device is a fastening band. The band is manufactured from a mechanically active shape memory material. The heads of the band are fastened together by a nail or another method. The band contracts according to the material programming towards the evolved shape which corresponds to the original non-oriented shape.

FIGS. 24a and 24b show a perspective view of a medical device for fracture fixation of soft tissue fixation to the bone. FIG. 24a shows the medical device in its initial shape before implantation. After implantation, the scales 5 of the implant are raised due to the mechanical shape memory, thus enhancing the fixation of the device as shown in FIG. 24b.

FIGS. 25a and 25b show the cross-section of a medical device, and FIGS. 26a and 26b show a perspective view of the medical device of FIGS. 25a and 25b. In these drawings, the medical device is a medical stent device having mechanically active shape memory properties. The mechanically active shape memory stent is delivered to a blood vessel or to another tubular structure that is to be kept open, for example the gall duct, by an endoscopic instrument. When the stent is released from the instrument, it will expand to its normal dimensions. This is the normal case of the delivery process of biodegradable stents. However, the stents manufactured from biodegradable dimensionally stable polymers might have poor expanding properties after longer storage times. When components manufactured from mechanically active shape memory polymers are incorporated in the stent structure, the stent will be able to expand more than the stents manufactured from dimensionally stable polymers. The stents are able to maintain the expanded shape due to the mechanically active shape memory components which are incorporated in the stent structure. The stent is also able to generate a predefined force of expansion due to the predetermined tension applied to at least part of the filaments of the stent in the manufacturing process and is thus capable of opening the tubular structure even more after the mechanical shape memory effect has been initiated in the implantation site.

FIGS. 27a and 27b show a suture anchor having a mechanical shape memory. The mechanical shape memory is activated in physiological environment. The diameter of the suture anchor expands as the length decreases (see FIG. 27b). The grooved shape provides the initial locking to the bone and the expansion of the diameter provides a permanent locking effect on the bone.

The suture anchor comprises an elongated shaft 12 and a tapering tip 11. The shaft 12 may be provided with ridges 10. In the shaft 12 near the tip 11 there is at least one hole 14 for a yarn 13.

FIG. 28 shows a screw comprising a head 15 and an elongated shaft 16 provided with threads. As in the case of the above-mentioned suture anchor, the shaft of the screw also has a mechanical shape memory and the shaft of the screw expands as the length decreases.

FIG. 29 shows a diagram on the effect of L-lactide monomer (auxiliary component) content on the dimensional changes in physiological conditions. The content of auxiliary component can be used to adjust the rate and extent of the mechanical activity. The tests are carried out by placing the samples freely in a phosphate buffer solution at 37° C. and periodically measuring the dimensions manually using a slide gauge.

The basic material is PLGA 85L/15G. The auxiliary agent in this case is L-lactide monomer. It can be clearly seen that increasing the monomer content yields an increasing speed and an increasing extent of dimensional changes. The materials are melt processed varying parameters between the samples but the deformation process of different samples is similar. Thus, the differences between the samples are due to the differences in the melt processing. The monomer can be fed into the extruder and mixed with the polymer, or the monomer can be generated in the material by increasing the processing temperature to a level which enables spontaneous monomer generation through thermal degradation of the polymer.

FIG. 30 shows a diagram on the effect of blending of dimensionally stable and dimensionally unstable polymers on the dimensional changes in physiological conditions. The PLA 50L/50D acts as a dimensionally unstable material and PLGA 85L/15G as a dimensionally stable material in this test. Pure PLA 50L/50D shows a fast dimensional change and a large extent of dimensional change. Melt mixing (blending) PLGA 85L/15G with PLA 50L/50D impedes both the rate and extent of the dimensional change. Increasing the content of PLGA 85L/15G yields a dimensional change that is slower and has a smaller extent.

FIG. 31 shows a diagram on the dimensional changes of PLA 50L/50D and PLGA 85L/15G blends. Thus, FIG. 29 represents a closer view of the two blends with 50% and 75% PLA 50L/50D content.

The data in FIG. 31 suggests that increasing the PLA 50L/50D content yields increasingly aggressive dimensional changes in physiological conditions. The process steps following the melt process have been similar in all samples, which shows that the effect is truly due to the composition of the mixture.

FIG. 32 shows a diagram on the effect of the deformation force on the residual force in stress relaxation testing. The samples are produced by using the free drawing method. The samples are fastened at both ends, heated for a specific time to a temperature above the glass transition temperature and drawn along the longitudinal axis to about 4 times the original length. The drawing force is measured during the deformation process, and the maximum value is represented in the graph for each sample. It can clearly be seen that the residual stress level nicely follows the deformation force level. After 7 days at 37° C. in phosphate buffer saline, drawing forces of 140 N, 93 N and 54 N yield residual relaxation forces of 125 N, 99 N and 67 N, whereas the used temperature ranges in the drawing process were from 57 to 62° C., from 68 to 73° C. and from 85 to 90° C., respectively.

FIG. 33 presents the mechanical shape memory effect and the factors which have an effect on it. The results of the tests show that the mechanical shape memory is activated in a physiological environment. If the tests are performed in dry conditions but at a physiological temperature (37° C.), no mechanical shape memory effect is detected. If the tests are performed in an aqueous environment but at room temperature (21° C.), no mechanical shape memory effect is detected. Thus, the stimulus for the mechanical shape memory effect is not the effect of liquid as such or the effect of the temperature as such but the synergy of temperature and liquid in the physiological conditions.

EXAMPLE 1

PLA 50D/50L is melt extruded to a round profile having a diameter of 6.45 mm using a 20 mm twin screw extruder. The extrusion temperatures are between 50° C. and 280° C. The throughput is 700 g/h. The 6.45 mm rod is then die drawn at 80° C. to a 3.40 mm rod having a grooved surface and subsequently cooled down to room temperature. The resulting draw ratio is 4. The billet has now the mechanical activity properties described in FIG. 1. A medical device represented in FIG. 18 and FIG. 19 is made out of this billet. First, a 30 mm long piece is cut out of this billet and one end is machined to form a sharp angle. The thinner section is made by machining. The head is compression molded at 110° C. and subsequently cooled down to room temperature. The function of this medical device in bone fixation application is represented in FIGS. 20 and 21.

EXAMPLE 2

A blend of PLGA 85L/15G and PLA 50D/50L is injection molded to a predefined shape for a biodegradable band for closure of sternotomy. The pre-shape is then free drawn at 78° C., wherein this temperature lies between the glass transition temperature and the melting temperature of the material. The final shape and details are machined after the orientation process. The oriented band is implanted around the sternum to close the sternotomy. The compression of the polymer band generates a predefined compression force in the sternotomy as shown in FIG. 1. Five to seven such bands are used in one sternotomy closure. The mechanism for the contraction of the band is shown in FIG. 23.

EXAMPLE 3

A device for distraction osteogenesis is shown in FIG. 16 and in FIG. 17. The frame structure is extruded and machined or injection molded from PLA 96L/4D and a contractile and expandable active component having mechanical activity shown in FIG. 1 is extruded and drawn from PLA 70L/30DL with L-lactide auxiliary component. The device is implanted to the distraction site and fixed to the bone using bioabsorbable screws. The device generates a predefined force level as described in FIG. 1 and a predefined contraction-expansion behavior as described in FIG. 28, FIG. 29 and FIG. 30.

EXAMPLE 4

A drillable pin for bone fracture fixation is shown in FIG. 13 and FIG. 14. A preform is extruded from a blend of PLGA 85L/15G and PLA 50D/50L to a grooved continuous form following die drawing to a round continuous form. The temperatures used in the extrusion process are between 50° C. and 260° C. The orientation temperature in the die drawing process lies between the glass transition temperature and the melting temperature of the blend. The pin is machined to the final product form and is gamma sterilized. The pin is drilled into the cancellous bone or compact bone using a predrilled hole. The round and smooth surfaced pin will initiate the shape transformation after implantation. The locking of the device to the bone is enhanced as the diameter of the device expands due to the device contracting and pulling the bone fragments tighter together as shown in FIG. 20 and FIG. 21. The grooved shape to which the device changes its shape in the drill hole generates a better torque resistance than round shaped devices. This stabilizes the fracture site, still enabling the surgeon to drill the device into the bone.

EXAMPLE 5

A medical fastener for bone fracture fixation of soft tissue attachment is shown in FIG. 22a. The device comprises of a fastener made of PLGA 85L/15G by extrusion and orientation, and a mechanically active component extruded and drawn from PLA 50D/50L. The fastener is machined to its final form before use, and the drawn and machined mechanically active part is attached to the bulk part. For both of the components, the extrusion temperatures are between 50° C. and 260° C. and the drawing temperatures are between the glass transition temperature and the melting temperature of each material. The fastener is gamma sterilized. After implantation, the fastener is activated due to the physiological environment. After the activation the mechanically active shape memory component starts to contract and the dimensionally stable component starts to open, due to the opening force generated by the contracting active component, thus enhancing the stability of the fixation as shown in FIG. 22b.

The invention claimed is:

1. A biodegradable orthopedic nail for bone fracture fixation consisting of:
    a head and an elongated shaft forming one continuous piece, wherein
    the elongated shaft consists of a smooth area, a longitudinally grooved area and a tapered tip,
    the smooth area being located adjacent to the head and the grooved area being located between the smooth area and the tapered tip, and
        wherein the smooth area, the grooved area and the tip are made of same polymeric material, said polymeric material having an oriented polymer structure so as to have a predetermined tension level of between 5N and 250N;
    the nail having an initial shape and at least one evolved shape, and the initial shape being adapted to change towards the at least one evolved shape due to an external stimulus, wherein the change includes a full length longitudinal shrinking of the elongated shaft and a full length radial expansion of the elongated shaft such that the full length longitudinal shrinking of the nail pulls the bone fragment together thereby tightening the bone fragment fixation, and wherein the external stimulus is an aqueous environment and temperature of 35° C. to 42° C.

2. The biodegradable orthopedic nail according to claim 1, wherein the nail is adapted to restore its tension to the predetermined tension level by the change of dimensions and by reducing the tension level if the bone fragment fixation is too tight or too loose.

3. The biodegradable orthopedic nail according to claim 1, wherein the nail has a predetermined rate of changing from the initial shape towards the at least one evolved shape.

4. The biodegradable orthopedic nail according to claim 1, wherein the nail has a predetermined shape between the initial shaped and the at least one evolved shape until which it changes toward the evolved shape.

5. The biodegradable orthopedic according to claim 1, wherein the nail comprises the at least one homopolymer, a copolymer, or a polymer blend.

6. The biodegradable orthopedic nail according to claim 5, wherein the nail comprises a blend of a copolymer or lactide and glycolide and a copolymer of D-lactide and L-lactide.

7. The biodegradable orthopedic nail according to claim 6, wherein the copolymer of lactide and glycolide comprises from 5 wt-% to 95 wt-% of lactide and from 95 wt-% to 5 wt-% of glycolide.

8. The biodegradable orthopedic nail according to claim 6, wherein the copolymer of D-lactide and L-lactide comprises from 3 wt-% to 98 wt-% of D-lactide and from 98 wt-% to 2 wt-% of L-lactide.

9. The biodegradable orthopedic according to claim 1, wherein the monomers comprise L-lactide.

* * * * *